(12) United States Patent
Takeuchi et al.

(10) Patent No.: US 12,344,825 B2
(45) Date of Patent: Jul. 1, 2025

(54) CULTURE METHOD

(71) Applicants: THE UNIVERSITY OF TOKYO, Tokyo (JP); TOYOTA BOSHOKU KABUSHIKI KAISHA, Aichi (JP)

(72) Inventors: Shoji Takeuchi, Tokyo (JP); Kanae Sakai, Aichi (JP)

(73) Assignees: THE UNIVERSITY OF TOKYO, Tokyo (JP); TOYOTA BOSHOKU KABUSHIKI KAISHA, Aichi (JP)

( * ) Notice: Subject to any disclaimer, the term of this patent is extended or adjusted under 35 U.S.C. 154(b) by 542 days.

(21) Appl. No.: 17/619,136

(22) PCT Filed: May 25, 2020

(86) PCT No.: PCT/JP2020/020481
§ 371 (c)(1),
(2) Date: Dec. 14, 2021

(87) PCT Pub. No.: WO2020/255637
PCT Pub. Date: Dec. 24, 2020

(65) Prior Publication Data
US 2022/0298460 A1    Sep. 22, 2022

(30) Foreign Application Priority Data
Jun. 17, 2019 (JP) .................... 2019-111807

(51) Int. Cl.
| C12N 1/20 | (2006.01) |
| C12M 1/00 | (2006.01) |
| C12M 1/32 | (2006.01) |
| C12N 1/14 | (2006.01) |
| C12N 1/16 | (2006.01) |

(52) U.S. Cl.
CPC ............ *C12M 23/12* (2013.01); *C12M 23/22* (2013.01); *C12M 23/38* (2013.01); *C12N 1/20* (2013.01)

(58) Field of Classification Search
CPC ......... C12M 23/12; C12M 23/22; C12N 1/20; C12N 1/14; C12N 1/16
See application file for complete search history.

(56) References Cited

U.S. PATENT DOCUMENTS

| 7,846,717 | B2 | 12/2010 | Yasuda et al. |
| 9,121,003 | B2 | 9/2015 | Nakazawa et al. |
| 10,030,221 | B2 | 7/2018 | Chan et al. |
| 10,914,725 | B2 | 2/2021 | Abe et al. |
| 2006/0014273 | A1 | 1/2006 | Yasuda et al. |
| 2011/0003389 | A1* | 1/2011 | Nakazawa ............ C12N 5/067 435/305.2 |
| 2015/0147768 | A1 | 5/2015 | Chan et al. |
| 2018/0136196 | A1 | 5/2018 | Abe et al. |

FOREIGN PATENT DOCUMENTS

| CN | 1678732 | 10/2005 |
| CN | 101629136 | 1/2010 |
| CN | 107532143 | 1/2018 |
| JP | 2000-197479 | 7/2000 |
| JP | 2005-27598 | 2/2005 |
| JP | 2005-224123 | 8/2005 |
| JP | 2005-261339 | 9/2005 |
| JP | 2007-111023 | 5/2007 |
| JP | 2015-136318 | 7/2015 |
| WO | 2009/034927 | 3/2009 |

OTHER PUBLICATIONS

Gokaltun et al. Simple Surface Modification of Poly(dimethylsiloxane) via Surface Segregating Smart Polymers for Biomicrofluidics. Sci Rep 9. 2019;7377:1-14.*
Eppendorf. Factors Influencing OD600 Measurements. https://www.eppendorf.com/product-media/doc/en/148369/Detection_White-Paper_027_BioPhotometer-D30_BioSpectrometer-family_Factors-Influencing-OD600-Measurements.pdf.2015;1-3.*
China Office Action recited in China Application No. 202080043809.6, dated Sep. 7, 2023.
Stefanie Siebenberg et al., "Reducing the variability of antibiotic production in Streptomyces by cultication in 24-square deepwell plates", Journal of Bioscience and Bioengineering, 109, 2010, dated Sep. 16, 2009 (available online), pp. 230-234.
Thomas Beneyton et al., "High-throughput screening of filamentous fungi using nanoliter-range droplet-based microfluidics", Scientific Reports, Jun. 7, 2016, pp. 1-10.
D. Nichols et al., "Use of Ichip for High-Throughtout In Situ Cultivation of "Uncultivable" Microbial Species", Applied and Enviromental Microbiology, vol. 76, No. 8 , Apr. 2010, pp. 2445-2450.
International Search Report issued in International Patent Application No. PCT/JP2020/020481, dated Jul. 28, 2020.
Japan Official Action received in Japanese Patent Application No. 2019-111807, dated Apr. 18, 2023.

* cited by examiner

*Primary Examiner* — Lynn Y Fan
(74) *Attorney, Agent, or Firm* — GREENBLUM & BERNSTEIN, P.L.C.

(57) ABSTRACT

Provided is a culture method for a microorganism using a plate-like microchamber having a plurality of wells independent from each other on a front surface thereof. The culture method for the microorganism includes: mixing a liquid culture medium containing agarose having a gelation temperature of no less than 5° C. and no more than 20° C. and the microorganism to obtain a mixture; enclosing the mixture into the well with the front surface facing upward; and keeping the microchamber in which the mixture is enclosed in the well at a predetermined temperature range.

6 Claims, 11 Drawing Sheets

CULTURE METHOD

TECHNICAL FIELD

The present disclosure relates to a culture method.

BACKGROUND ART

As methods for culturing a microorganism, the following methods are known for example (see Non-Patent Literatures 1 to 3).

Non-Patent Literature 1 discloses a method for culturing an actinomycete as a microorganism in a deep well plate.

Non-Patent Literature 2 discloses a culture method in which an *Aspergillus* mold as a microorganism is enclosed and cultured in a fluorine-based oil together with a culture medium. In this culture method, Water-in-oil microdroplet (droplet in oil) is used.

Non-Patent Literature 3 discloses a method in which a plate-like device having small holes is sandwiched between semipermeable membranes, and nutrients in the surrounding environment are incorporated and cultured.

CITATIONS LIST

Non-Patent Literature

Non-Patent Literature 1

S. Siebenberg et al. Journal of Bioscience and Bioengineering 2010. 109 (3). 230-234 Non-Patent Literature 2:

T. Beneyton et al. Scientific Reports 2016. 7. 27223 Non-Patent Literature 3:

D. Nichols et al. Applied and Environmental Microbiology 2010. 76(8). 2445-2450

SUMMARY OF INVENTION

Technical Problems

However, the conventional culture methods are not necessarily sufficient in practice as methods for culturing a plurality of samples (microorganisms) in a state of being independent from each other, and a new culture method has been desired.

The present invention has been made in view of the above circumstances, and it is an object of the present invention to provide a new culture method capable of culturing a plurality of samples in a state of being independent from each other.

Solutions to Problems

As a result of intensive studies, the inventors of the present invention have developed a novel method for culturing a microorganism.

It has been found that the problems of the conventional methods can be solved according to this method, and that a plurality of samples can be cultured in a state of being independent from each other. The following invention is provided based on this finding.

[1] A culture method for a microorganism using a plate-like microchamber having a plurality of wells on a front surface thereof, the wells being independent from each other, the method including:

a step of mixing a liquid culture medium containing agarose having a gelation temperature of no less than 5° C. and no more than 20° C. and the microorganism to obtain a mixture;

a step of enclosing the mixture having a temperature higher than the gelation temperature of the agarose into the well with the front surface facing upward; and a step of keeping the microchamber in which the mixture is enclosed in the well at a predetermined temperature range.

Advantageous Effects of Invention

In the culture method for a microorganism of the present disclosure, a plate-like microchamber having a plurality of wells independent from each other is used. The microorganism is cultured in a state of being enclosed in the well together with agarose. Because the wells are independent from each other, the microorganism enclosed in each well can be cultured in an independent state without being mixed with any other.

Furthermore, the liquid culture medium contains agarose having a gelation temperature of no less than 5° C. and no more than 20° C. A sol of the mixture may be obtained by warming the mixture up to a temperature at which the microorganism is not destroyed, and this sol can be put into a well. Thus, the mixture can be easily put into the well.

DESCRIPTION OF EMBODIMENTS

Here, desirable examples of the present disclosure will be described.

[2] The culture method according to [1], wherein a sol of the mixture is pushed into the well with a plate member when the mixture is enclosed into the well. By pushing the sol of the mixture into the well with the plate member, the mixture can be sufficiently enclosed in the well.

[3] The culture method according to [1] or [2], wherein a bottom surface of the well is flat, and when a culture state of the microorganism is checked, the check is made by observing the microorganism being present on the bottom surface from a back surface side of the microchamber. If the microorganism is observed from the front surface side, it may be difficult to observe the microorganism because unevenness may be present on the surface of the mixture containing the microorganism. In the present configuration, however, the observation is easy because the microorganism being present on the flat bottom surface is observed from the back surface side of the microchamber.

Hereinafter, the present disclosure will be described in detail. In the notation indicating a range of "x to y", x and y are included in the range unless otherwise specified. That is, in the description using "to" for a numerical range, the lower limit and the upper limit are included unless otherwise specified. For example, the expression "10 to 20" includes both the lower limit value "10" and the upper limit value "20". That is, "10 to 20" has the same meaning as "no less than 10 and no more than 20".

1. Explanation of Terms of Culture Method for Microorganism 13

In the culture method for the microorganism 13 of the present disclosure, a plate-like microchamber 3 having a plurality of wells 1 independent from each other on a front surface 3A is used. The culture method for the microorganism 13 includes a step of mixing a liquid culture medium 11 containing agarose having a gelation temperature of no less than 5 and no more than 20° C. and the microorganism 13 to obtain a mixture 15, a step of enclosing the mixture 15 into the well 1 with the front surface 3A facing upward, and a step of keeping the microchamber 3 in which the mixture 15 is enclosed in the well 1 at a predetermined temperature range.

(1) Microorganism 13

The type of the microorganism 13 is not particularly limited. Examples of the microorganism 13 include bacteria such as actinomycetes, *Escherichia coli*, and *Bacillus subtilis*, fungi such as mold and yeast, microalgae such as Cyanobacteria, and Labyrinthulea.

(2) Microchamber 3

The microchamber 3 is a plate-like member having a plurality of wells 1 as depressions on the front surface 3A.

The material of the microchamber 3 is not particularly limited. As the material, for example, a silicone resin is suitably used. The silicone resin is not particularly limited, and polydimethylsiloxane (PDMS), polymethylphenylsiloxane, polymethylhydrogensiloxane, polymethylmethoxysiloxane, polymethylvinylsiloxane and the like are preferred. One kind of these silicone resins may be used alone, and two or more kinds may be used in combination. Polydimethylsiloxane (PDMS) is particularly preferred because it is transparent, and the culture state of the microorganism 13 in the well 1 can be easily checked from the back surface 3B side of the microchamber 3.

The planar shape and size of the microchamber 3 are not particularly limited.

The planar shape of the microchamber 3 may be, for example, a rectangular shape, a circular shape, or the like.

When the planar shape of the microchamber 3 is rectangular, the size of the microchamber 3 is preferably no less than 5 mm×10 mm, more preferably no less than 7 mm×12 mm, and further preferably no less than 10 mm×15 mm, from the viewpoint of handleability and productivity. On the other hand, the size of the microchamber 3 is preferably no more than 35 mm×40 mm, more preferably no more than 33 mm×38 mm, and further preferably no more than 25 mm×30 mm, from the viewpoint of handleability and productivity. From these viewpoints, when the planar shape of the microchamber 3 is rectangular, the size of the microchamber 3 is preferably 5 mm×10 mm to 35 mm×40 mm, more preferably 7 mm×12 mm to 33 mm×38 mm, and further preferably 10 mm×15 mm to 25 mm×30 mm.

The thickness t1 (see FIG. 2) of the microchamber 3 is not particularly limited.

The thickness t1 of the microchamber 3 is preferably no less than 350 µm, more preferably no less than 400 µm, and further preferably no less than 450 µm, from the viewpoint of sufficiently securing the depth 1C of the well 1. On the other hand, the thickness t1 of the microchamber 3 is preferably no more than 650 µm, more preferably no more than 600 µm, and further preferably no more than 550 µm, from the viewpoint of handleability and productivity. From these viewpoints, the thickness t1 of the microchamber 3 is preferably 350 µm to 650 µm, more preferably 400 µm to 600 µm, and further preferably 450 µm to 550 µm.

The microchamber 3 is preferably hydrophilized from the viewpoint that the mixture 15 of the microorganism 13 and the liquid culture medium 11 can be smoothly enclosed into the well 1. The hydrophilization treatment is not particularly limited. For example, a hydrophilization treatment with an $O_2$ asher is suitably employed.

(3) Well 1

The planar shape and size of well 1 are not particularly limited.

As the planar shape of the well 1, for example, a circular shape, a rectangular shape, or the like may be employed. The planar shape of the well 1 is preferably circular from the viewpoint that the mixture 15 can be smoothly enclosed in the well 1.

Regarding the size of the well 1, when the planar shape of the well 1 is circular, the diameter 1A (see FIG. 2) is preferably no less than 350 µm, more preferably no less than 400 µm, and further preferably no less than 450 µm, from the viewpoint of sufficiently securing a culture space for the microorganism 13. On the other hand, regarding the size of the well 1, the diameter 1A is preferably no more than 650 µm, more preferably no more than 600 µm, and further preferably no more than 550 µm, from the viewpoint of simultaneously evaluating more samples. From these viewpoints, when the planar shape of the well 1 is circular, the diameter 1A is preferably 350 µm to 650 µm, more preferably 400 µm to 600 µm, and further preferably 450 µm to 550 µm.

The inter-well distance 1B (see FIG. 2) is not particularly limited.

The inter-well distance 1B is preferably no less than 100 µm, more preferably no less than 120 µm, still and further preferably no less than 150 µm, from the viewpoint of culturing the microorganism 13 in each well 1 in an independent environment. On the other hand, the inter-well distance 1B is preferably no more than 300 µm, more preferably no more than 280 µm, and further preferably no more than 250 µm, from the viewpoint of simultaneously culturing more of the microorganism 13. From these viewpoints, the inter-well distance 1B is preferably 100 µm to 300 µm, more preferably 120 µm to 280 µm, and further preferably 150 µm to 250 µm.

The inter-well distance 1B corresponds to the thickness of the wall partitioning the adjacent wells 1.

The depth 1C (see FIG. 2) of the well 1 is not particularly limited.

Figure 1:
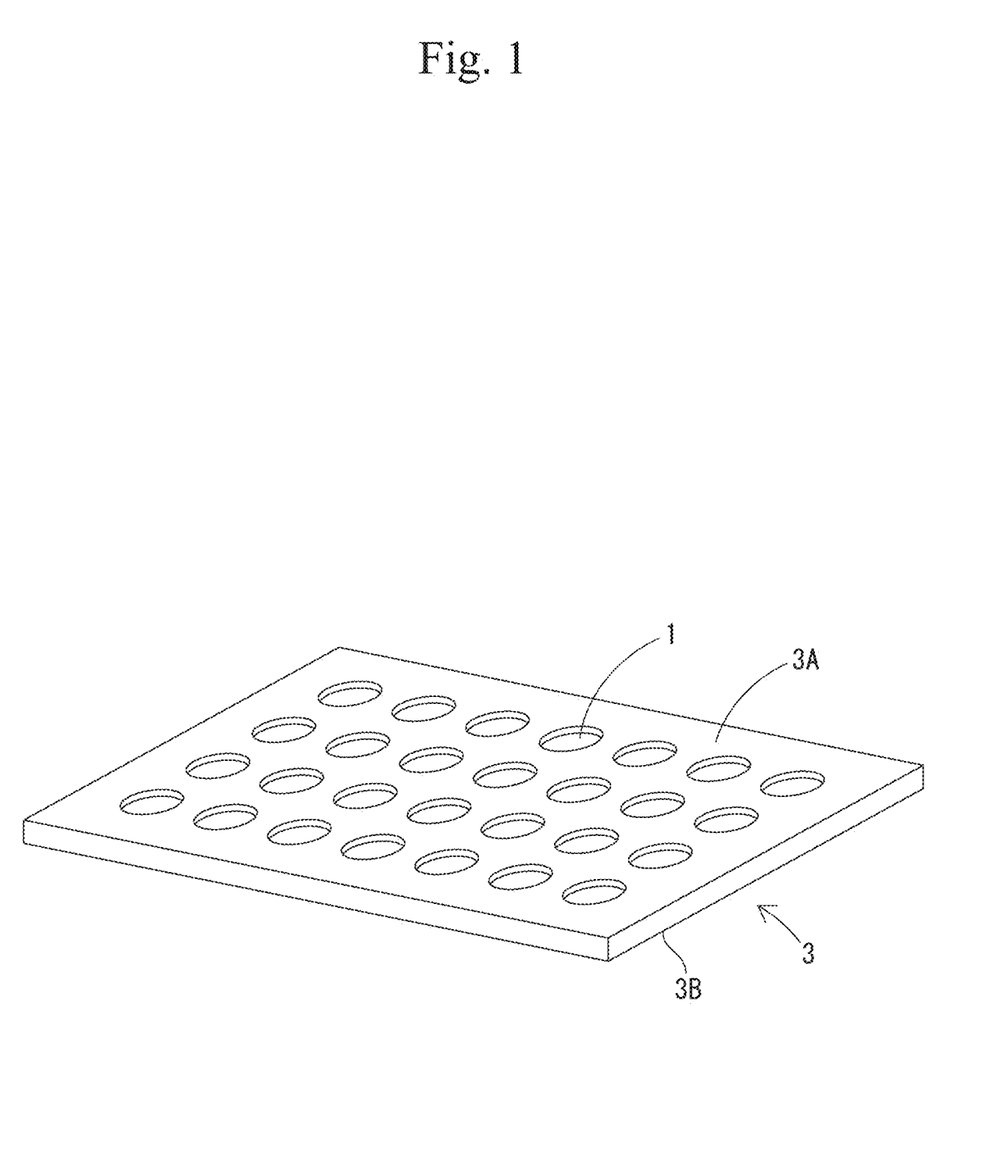
FIG. 1 is a perspective view showing an example of a microchamber.
Figure 2:
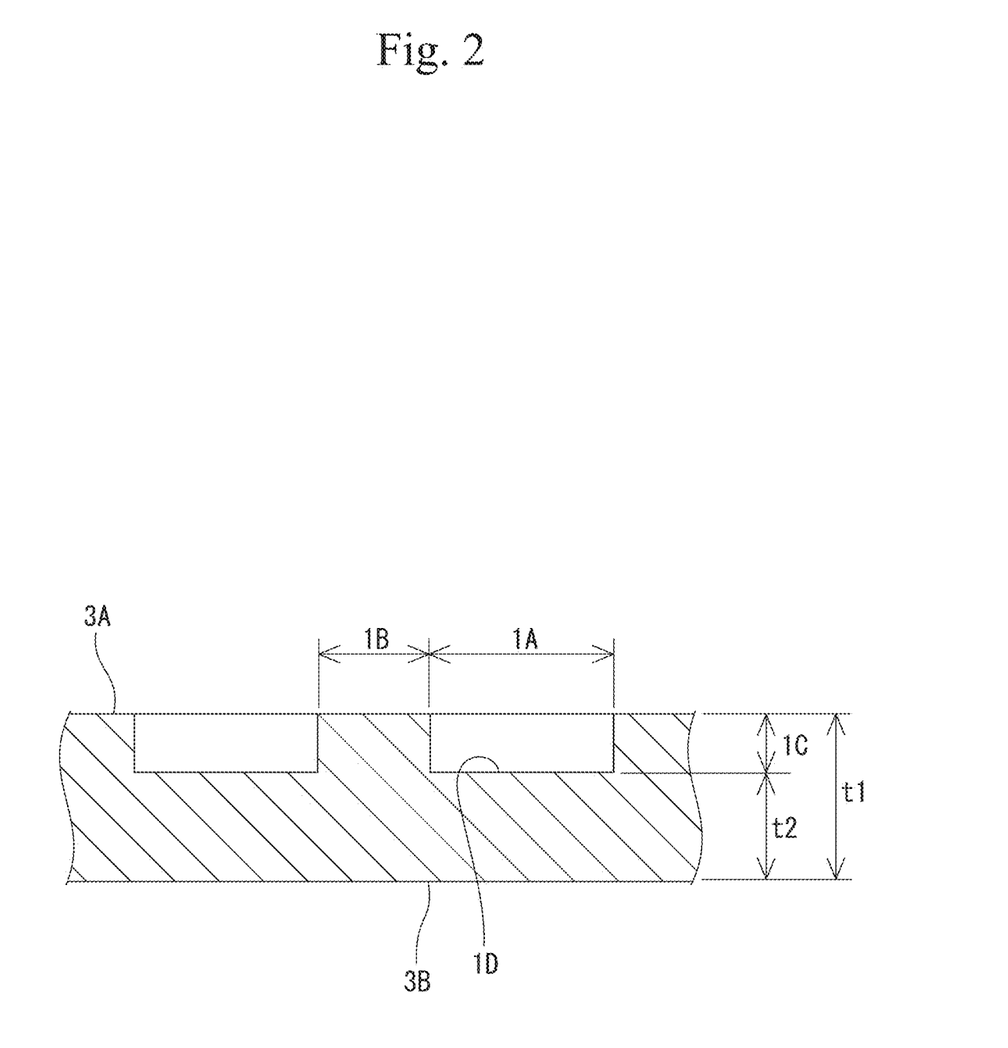
FIG. 2 is a cross-sectional view showing an example of a well.

The depth 1C of the well 1 is preferably 40 µm to 160 µm, more preferably 60 µm to 140 µm, and further preferably 80 µm to 120 µm, from the viewpoint of sufficiently securing a culture space for the microorganism 13 in the well 1. When the depth 1C of the well 1 is not constant, a value at the deepest place is adopted as the depth 1C of the well 1 in the present specification.

The thickness t2 (see FIG. 2) of the microchamber 3 at the portion where the well 1 is formed, that is, the distance from the bottom surface 1D of the well 1 to the back surface 3B is not particularly limited. The thickness t2 of the microchamber 3 is preferably no more than 600 µm, and more preferably no more than 500 µm, from the viewpoint of easy observation through the microchamber 3 when the culture state of the microorganism 13 in the well 1 is observed from the back surface 3B side of the microchamber 3. On the other hand, the thickness t2 of the microchamber 3 is preferably no less than 300 µm, and more preferably no less than 350 µm, from the viewpoint of preventing breakage of the bottom surface 1D of the well 1. From these viewpoints, the thickness t2 of the microchamber 3 is preferably 300 µm to 600 µm, and more preferably 350 µm to 500 µm. When the thickness t2 is not constant, a value at the thickest (largest) part is adopted as the thickness t2 in the present specification.

The bottom surface 1D of the well 1 is desirably flat. When the bottom surface 1D is flat, it is easy to focus on and observe the microorganism 13 in observing the microorganism 13 near the bottom surface 1D from the back surface 3B side of the microchamber 3.

The number of wells 1 in one microchamber 3 is not particularly limited, and is appropriately selected according to the size of the microchamber 3 and the like.

For example, the number may be 100 to 10,000 per area of 20 mm×25 mm.

(4) Liquid Culture Medium 11

The liquid culture medium 11 contains agarose having a gelation temperature (gelation point) of no less than 5° C. and no more than 20° C. This agarose has a low gelation temperature and is also called low-melting-point agarose. The gelation temperature means a temperature at which a gel is formed as an agarose aqueous solution cools down.

The concentration of the agarose in the liquid culture medium 11 is not particularly limited.

From the viewpoint of prevention of evaporation, the concentration of agarose is preferably no less than 0.1% (w/v), more preferably no less than 0.5% (w/v), and further preferably no less than 0.7% (w/v). On the other hand, the concentration is preferably no more than 3.0% (w/v), more preferably no more than 2.0% (w/v), and further preferably no more than 1.5% (w/v), from the viewpoint of operability of sufficiently securing the fluidity of the mixture 15 to smoothly enclose the mixture 15 into the well 1. From these viewpoints, the concentration of the agarose is preferably 0.1% (w/v) to 3.0% (w/v), more preferably 0.5% (w/v) to 2.0% (w/v), and further preferably 0.7% (w/v) to 1.5% (w/v).

The liquid culture medium 11 usually contains a carbon source and a nitrogen source. As the carbon source, any commonly used carbon sources such as glucose, fructose, xylose, saccharose, maltose, soluble starch, molasses, glycerol, and mannitol may be used, and the carbon source is not limited to these sources. As the nitrogen source, not only natural nitrogen sources such as yeast extract, malt extract, peptone, meat extract, casamino acid, corn steep liquor, soybean protein, defatted soybean, and cottonseed residue, but also organic nitrogen sources such as urea and inorganic nitrogen sources such as sodium nitrate, ammonium nitrate, and ammonium sulfate may be used.

In addition, inorganic salts such as phosphate, magnesium sulfate, iron sulfate, and copper sulfate, vitamins, and the like may also be used as a trace nutrient source as necessary. These medium components are not particularly limited as long as they have a concentration that does not impair the growth of the microorganism 13. The content of the carbon source is preferably 0.1% to 10% (w/v). The content of the nitrogen source is preferably 0.1% to 5% (w/v).

The pH of the liquid culture medium 11 is preferably 4 to 10, and more preferably 5 to 9.

2. Description of Steps in Culture Method for Microorganism 13

(1) Mixing Step

Figure 3:
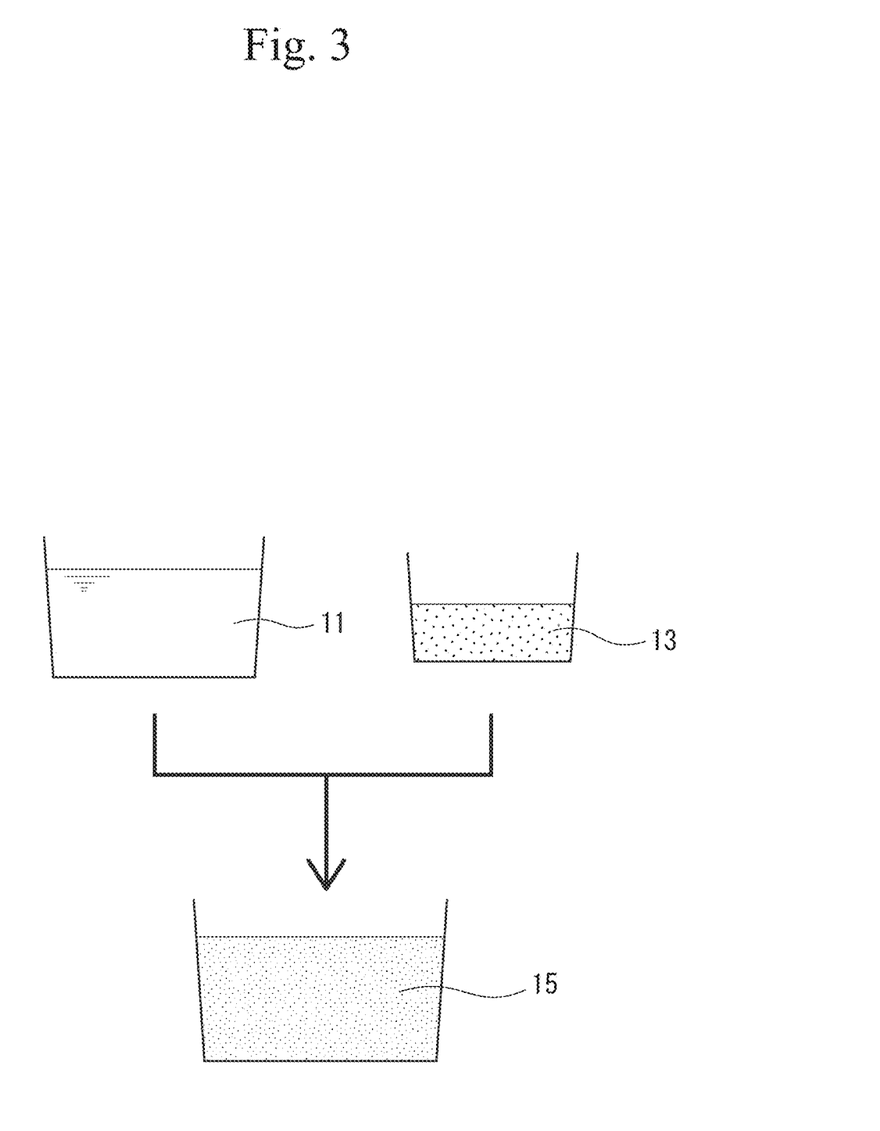
FIG. 3 is a conceptual diagram illustrating a mixing step.

In the mixing step, as exemplified in FIG. 3, the liquid culture medium 11 and the microorganism 13 are mixed to obtain the mixture 15.

The mixing ratio of the liquid culture medium 11 and the microorganism 13 is not particularly limited. From the viewpoint of facilitating the observation of the culture state of the microorganism 13, it is preferable to adjust the mixing ratio so that the turbidity (OD) of the microorganism 13 in the mixture 15 is 0.05 to 0.15, and it is more preferable to adjust the mixing ratio so that the turbidity is 0.08 to 0.12.

The "turbidity" in the present specification is the most common, and simple and rapid measurement method in which the growth of the microorganism 13 is measured by the degree of turbidity (amount of bacteria in culture solution) of a culture solution (here, the mixture 15 which is the liquid culture medium 11 containing the microorganism 13). Light is applied to the culture medium to measure how much the transmitted light is blocked by scattering and absorption. Because the microorganism 13 is fine particles, the amount of the microorganism 13 and the turbidity of the culture solution are in a proportional relationship. The turbidity is measured as follows for example.

Light of a single wavelength of 660 nm is made incident on the culture solution, and the transmitted light is measured with a spectrophotometer. Here, the absorbance obtained by the following formula is defined as the turbidity (OD) of the culture solution, wherein the intensity of the incident light is $I_0$, the intensity of the transmitted light is I, the thickness of the transmission layer is L, and the absorbance is $\tau$.

$$I = I_0 \text{Exp}(-\tau L) \qquad \text{[Formula 1]}$$

(2) Enclosing Step

Figure 4:
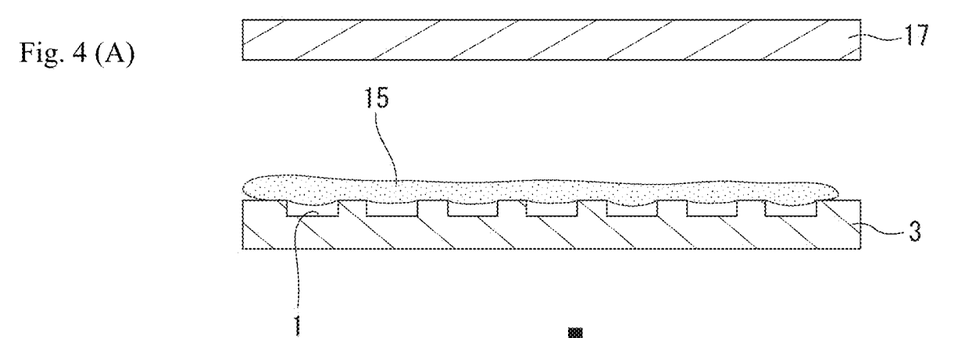
FIGS. 4(A)-(D) show a conceptual diagram illustrating an enclosing step.

In the enclosing step, the mixture 15 having a temperature higher than the gelation temperature of agarose is enclosed into the well 1 with the front surface 3A facing upward (see FIG. 4).

The temperature higher than the gelation temperature of agarose is preferably 20° C. to 40° C. and more preferably 30° C. to 37° C., from the viewpoint of making the mixture 15 into a sol without destroying the microorganism 13.

When the mixture 15 is enclosed in the well 1, it is preferred to push the mixture 15 into the well 1 with a plate member 17 from the viewpoint of sufficiently enclosing the mixture 15 into the well 1 (see FIGS. 4(A) and 4(B)).

The plate member 17 is not particularly limited, and for example, a glass plate may be employed. Using a glass plate allows the enclosed state (filled state) of the mixture 15 to be easily checked through the glass plate. The glass plate is preferably one in which organic substances and the like are removed by piranha cleaning using a piranha solution. Piranha solution is a mixture of sulfuric acid and hydrogen peroxide.

After the mixture 15 is enclosed in the well 1, water 16 may be added onto an upper surface 15A of the mixture 15 (see FIGS. 4(C) and 4(D)). Adding the water 16 in this manner keeps the mixture 15 in the incubation step from drying.

(3) Incubation Step

Figure 5:
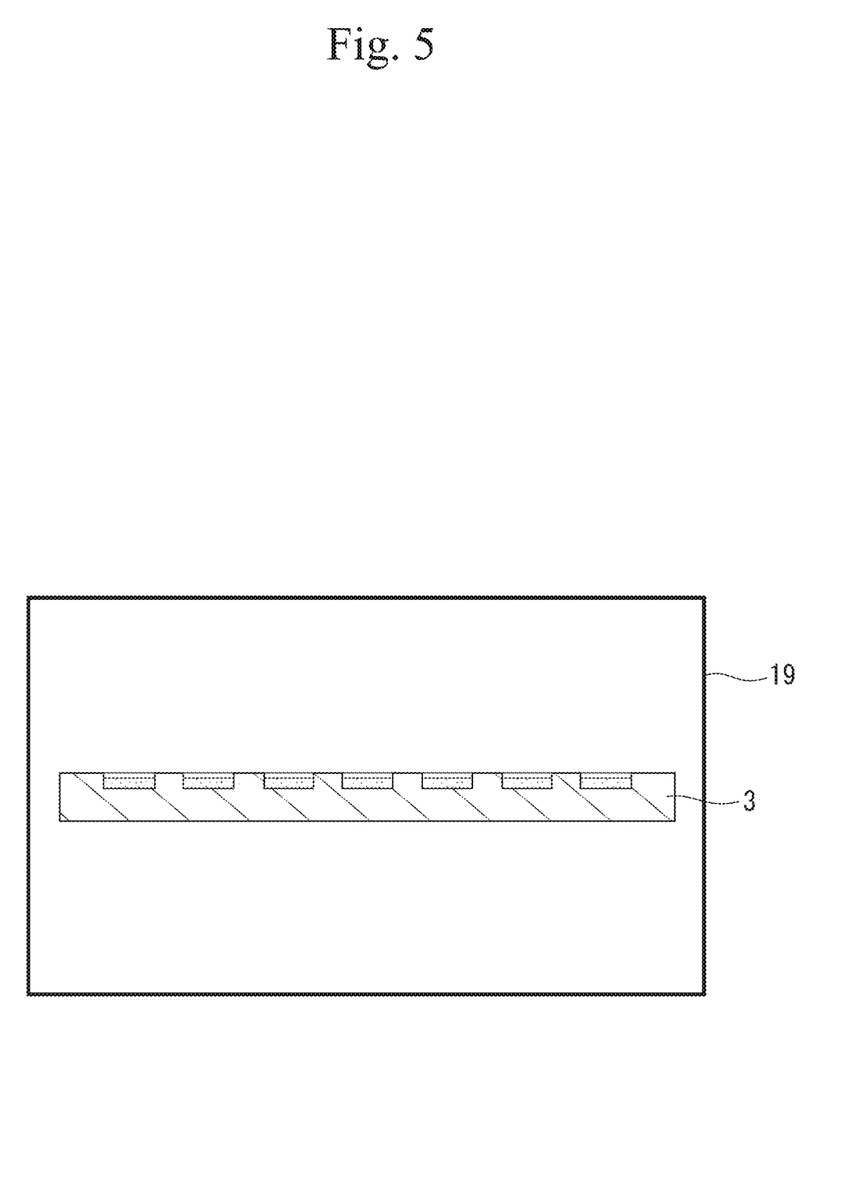
FIG. 5 is a conceptual diagram illustrating an incubation step.

In the incubation step, the microchamber 3 in which the mixture 15 is enclosed in the well 1 is kept at a predetermined temperature range (see FIG. 5).

The predetermined temperature range is appropriately selected according to the type of the microorganism 13, and is a temperature range suitable for culturing the microorganism 13. For example, in the case of actinomycetes, the temperature is 25° C. to 30° C.

In the incubation, a thermostatic bath 19 is used for example (see FIG. 5).

The time for the incubation at the predetermined temperature range is not limited to particular length, and may be appropriately changed depending on the microorganism 13. The time for the incubation is preferably 2 hours to 10 days, and more preferably 10 hours to 7 days.

(4) Growth State Check

Figure 6:
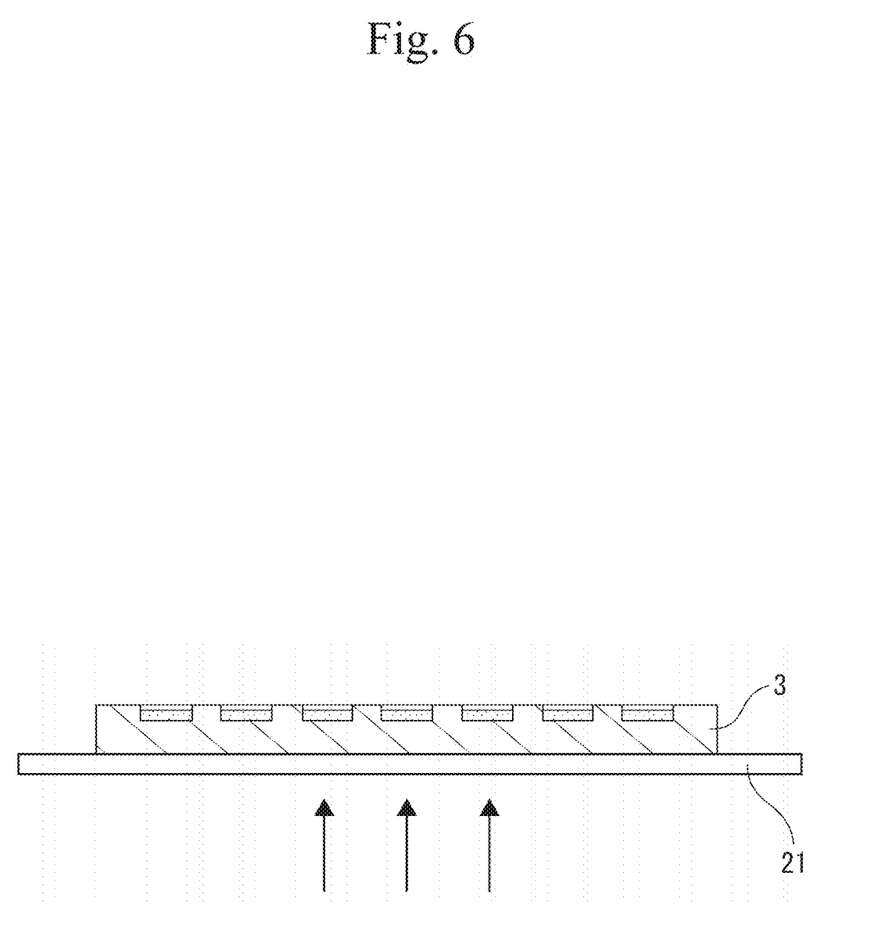
FIG. 6 is a conceptual diagram of an example of a method for checking a growth state.

In the culture method of the present disclosure, the growth state of the microorganism 13 may be checked. For example, as shown in FIG. 6, the growth state of the microorganism 13 can be checked by placing the microchamber 3 on a stage 21 of an inverted microscope, and observing the microchamber 3 from the lower side of the microchamber 3, that is, from the direction of the arrows in FIG. 6.

3. Effects of Present Embodiment

According to the culture method for the microorganism 13 of the present disclosure, the plate-like microchamber 3 having the plurality of wells 1 independent from each other is used. The microorganism 13 is cultured in a state of being enclosed in the well together with agarose. Because the wells 1 are independent from each other, the microorganism 13 enclosed in each well 1 can be cultured in an independent state without being mixed with any other.

EXAMPLES

Hereinafter, more specific description will be given with reference to Examples.

1. Fabrication of Microchamber 3

(1) Fabrication of Microchamber Mold

On a 2.5 inch silicon wafer, 1 mL of SU8-50 (resist, manufactured by Nippon Kayaku Co., Ltd.) was placed. After bubbles in the SU8-50 were removed, the SU8-50 was applied over the silicon wafer with a spin coater at a rotation speed of 1000 rpm. The silicon wafer coated with SU8-50 was sequentially heated at 65° C. for 15 minutes, heated at 95° C. for 40 minutes, and allowed to cool for one hour (cooled to 40° C. or lower). Thereafter, a chromium mask (mold) with a patterned microchamber was put on the silicon wafer coated with SU8-50, and the silicon wafer was exposed to light with a mask aligner for 19 seconds. Then, after a post bake at 65° C. for 2 minutes and 95° C. for 15 minutes, the silicon wafer was washed with SU8 developer and isopropyl alcohol and developed, whereby a microchamber mold of SU8 having a height of 100 μm was fabricated.

(2) Fabrication of Microchamber 3

A PDMS base and a curing agent were mixed at 10:1, and 5 g of the degassed solution was poured into the microchamber mold of SU8, vacuumed for 1 hour, and then cured at 75° C. for 2 hours. The mold of SU8 was removed from the cured PDMS, whereby a microchamber 3 (dimension 20 mm×25 mm) made of PDMS was obtained.

The planar shape of the well 1 was circular (diameter: 500 μm). The depth C1 of the well 1 was 100 μm, and the inter-well distance 1B was 200 μm. The number of wells was 500.

2. Culture of Microorganism 13

As the liquid culture medium 11, one having the following composition was used. As agarose, A2576 Agarose (Ultra-low Gelling Temperature, molecular biology grade, Sigma-Aldrich, gel point≤20° C.) was used.

As the microorganism 13, an actinomycete was used.

The liquid culture medium 11 and the microorganism 13 were mixed to obtain a mixture 15 (see FIG. 3). At this time, the liquid culture medium 11 and the actinomycete (microorganism 13) were mixed so that the turbidity (OD) of the actinomycete (microorganism 13) in the mixture 15 was 0.1.

The mixture 15 was incubated at 28° C.

Medium Composition

Yeast extract: 4 g
Malt extract: 10 g
Glucose: 4 g
Distilled water: 1 L
pH: 7.3
Agarose concentration: 1% (w/v)

The microchamber 3 made of PDMS was hydrophilized with an $O_2$ asher (125 W, 10 sec).

The mixture 15 in a sol state was placed on the microchamber 3 with the front surface 3A on which the wells 1 were formed facing upward. A glass plate (plate member 17) subjected to piranha cleaning was pressed against the front surface 3A of the microchamber 3 to pressurize the mixture 15, then the mixture 15 was enclosed into the wells 1 (see FIGS. 4(A) and 4(B)).

Thereafter, the glass plate (plate member 17) was removed, and water 16 (distilled water) was added onto an upper surface 15A of the mixture 15 (see FIGS. 4(C) and 4(D)).

Then, the microchamber 3 in which the mixture 15 is enclosed in the wells 1 was allowed to stand at 28° C., and the actinomycete (microorganism 13) was cultured (see FIG. 5).

When the culture time was 0 hours, 20 hours, and 7 days, the growth state of the actinomycetes (microorganism 13)

enclosed in the well 1 of the microchamber 3 was checked with an inverted microscope (see FIG. 6).

3. Evaluation Results

Figure 7:
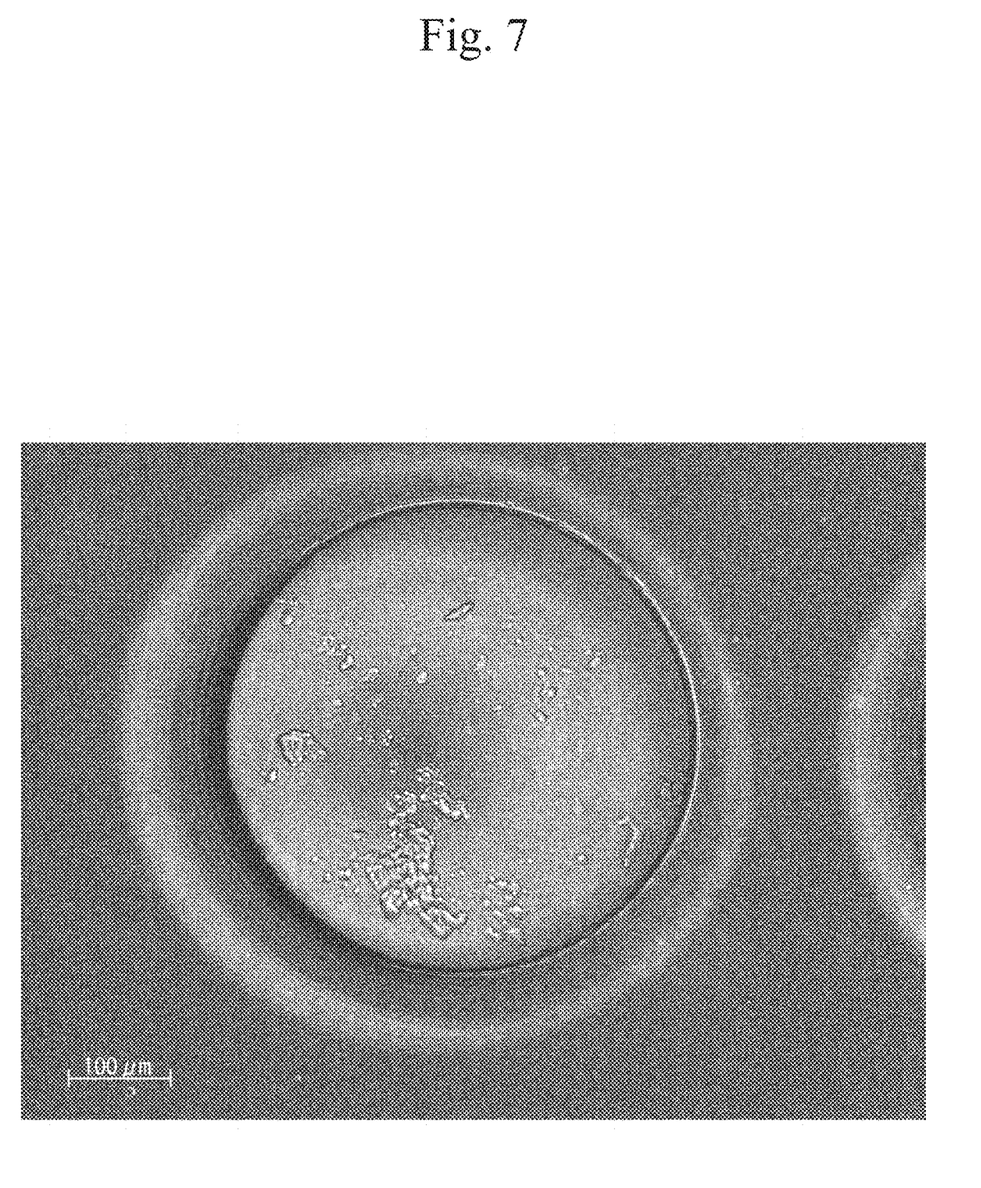
FIG. 7 is an observation image of a well at a culture time of 0 hours.
Figure 8:
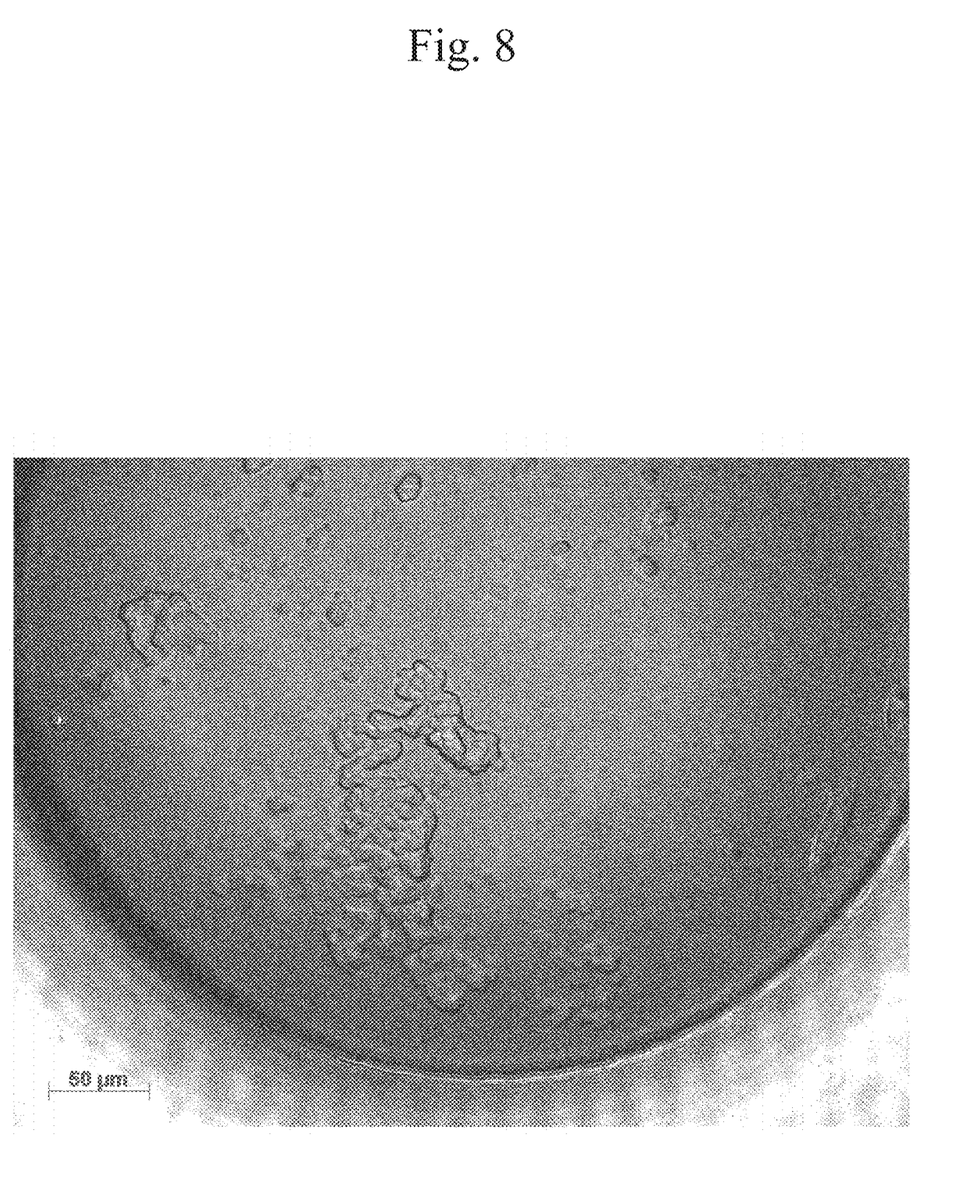
FIG. 8 is an observation image of a well at a culture time of 0 hours.
Figure 9:
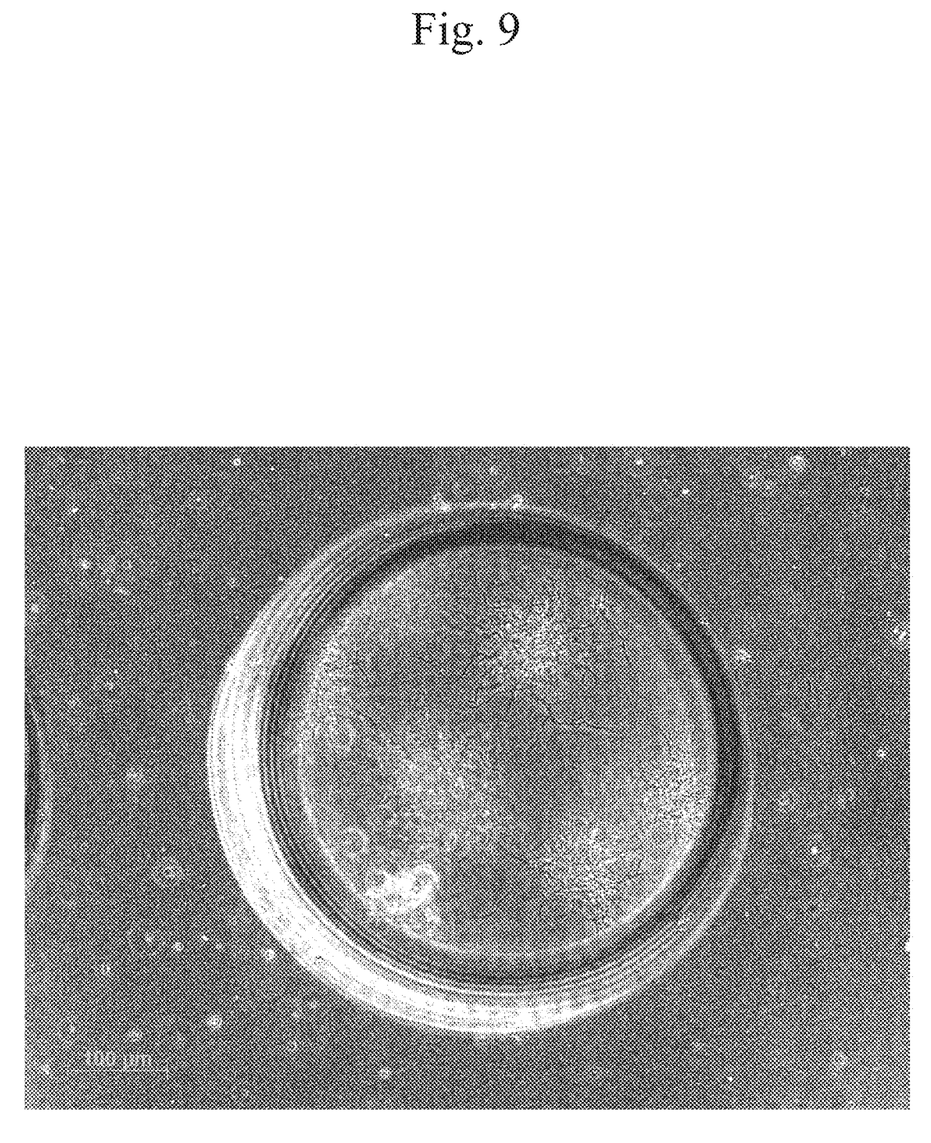
FIG. 9 is an observation image of a well at a culture time of 20 hours.
Figure 10:
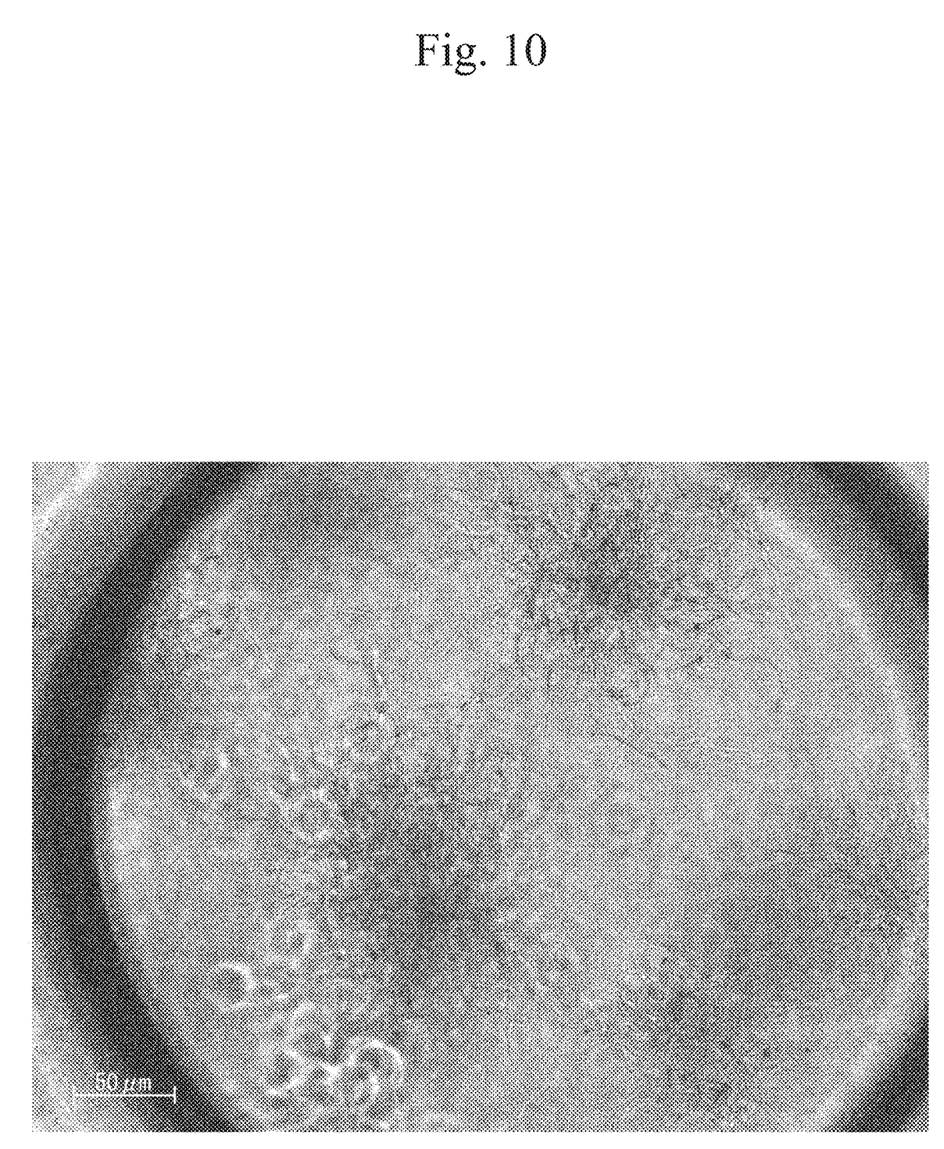
FIG. 10 is an observation image of a well at a culture time of 20 hours.

FIGS. 7 and 8 are observation images of the well 1 at the culture time of 0 hours. FIGS. 9 and 10 are observation images of the well 1 at the culture time of 20 hours. Comparing the observation image at the culture time of 0 hours and the observation image at the culture time of 20 hours, it can be seen that the hyphae are growing in a dendritic shape at the culture time of 20 hours. It can be seen that the hyphae are growing within the well 1 and do not protrude out of the well 1 even at the culture time of 20 hours.

Figure 11:
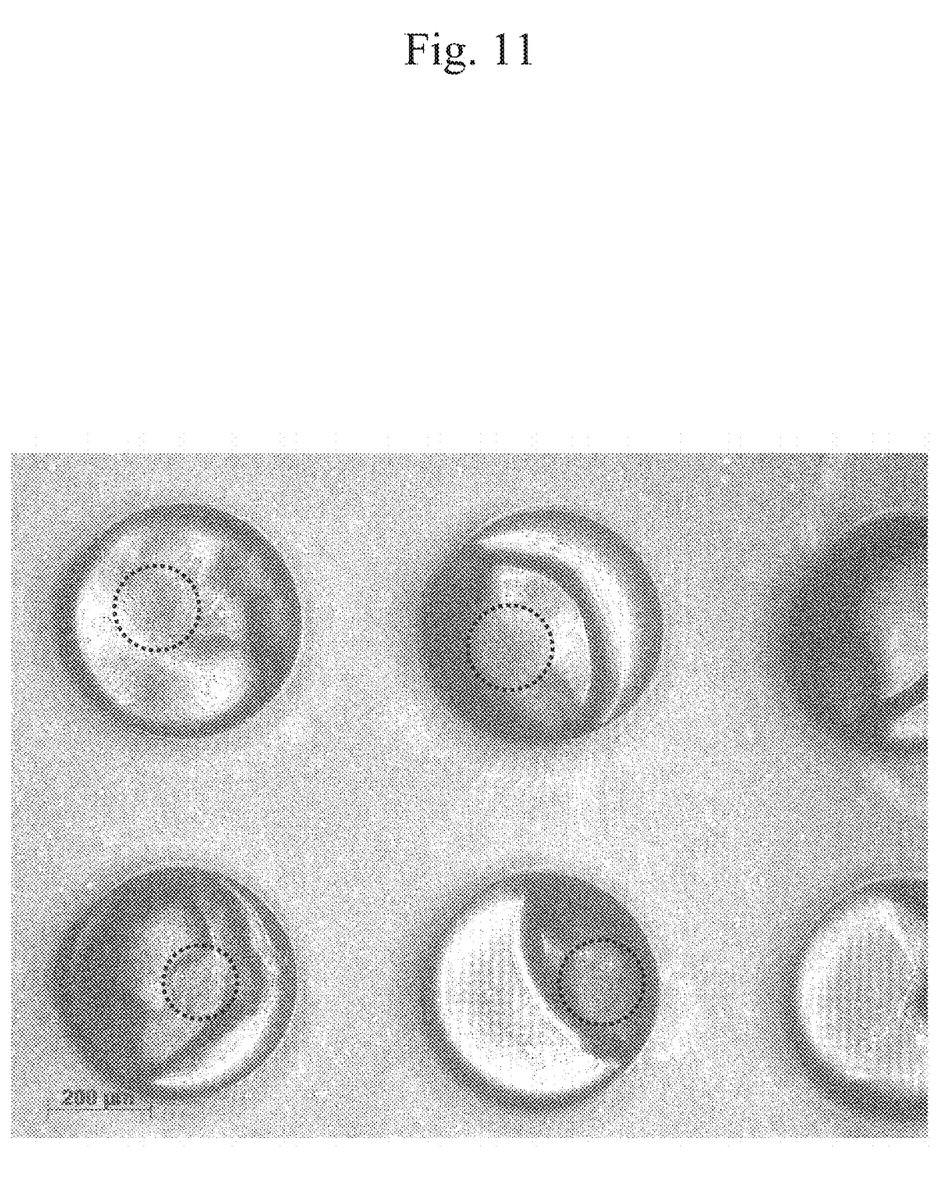
FIG. 11 is an observation image of wells at a culture time of 7 days.

FIG. 11 is an observation image of the well 1 at the culture time of 7 days. It was found that the hyphae were growing in a dendritic shape even at the culture time of 7 days. That is, an aggregate of hyphae was observed in an area surrounded by a round broken line in FIG. 11. As described above, it was found that the hyphae were growing within the well 1 and did not protrude out of the well 1 even at the culture time of 7 days. Therefore, in the culture method of this Example, it was confirmed that the microorganism 13 can be cultured in a chambered micro space for a long period of time (several days) even for a long period of 7 days.

In the Water-in-oil microdroplet (droplet in oil) method of Non-Patent Literature 2, the hyphae break the microdroplets after 32 hours from an extension of the hyphae, and thus the microorganism 13 cannot be cultured in a chambered micro space for a long period of time (several days).

In the IChip method of Non-Patent Literature 3, each microorganism 13 cannot be cultured in an independent environment because the compound produced by the chambered microorganism 13 permeates a semipermeable membrane and affects other microorganisms. In this method, when the device is taken out from the environment (soil or the like) and used in order to prevent leakage of the compound, the culture medium dries up, and thus long-term culture cannot be performed.

The culture method of this Example does not have the disadvantages of the Water-in-oil microdroplet (droplet in oil) method of Non-Patent Literature 2 and the IChip method of Non-Patent Literature 3. The culture method of this Example can culture the microorganism 13 in an independent state for a long period of time (several days) in a chambered micro space.

4. Effects of Example

According to the culture method of this Example, the microorganism 13 is cultured in a state of being enclosed in the well 1 together with agarose. Because the wells 1 are independent from each other, the microorganism 13 enclosed in each well 1 can be cultured in an independent state without being mixed with any other. Therefore, this culture method does not have the disadvantage of the Water-in-oil microdroplet (droplet in oil) method, that is, the disadvantage that the microorganism 13 protrudes outside the chamber. In addition, this culture method does not have the disadvantage of the IChip method (Non Patent Literature 3), that is, the disadvantage of leakage of the compound outside the chamber.

According to the culture method of this Example, 500 wells are arranged in the microchamber 3 having dimensions of 20 mm×25 mm. In the culture method of this Example, more samples can be cultured than in a conventional method because the microchamber 3 having a large number of wells 1 is used as described above. For example, assuming that only 96 samples can be cultured at the same time in a conventional method, about 5 times more samples can be cultured at the same time according to the culture method of this Example.

The foregoing example is for illustrative purposes only and is not to be construed as limiting the present invention. Although the present invention has been described with reference to exemplary embodiments, it is understood that the words used in the description and illustration of the present invention are illustrative and exemplary rather than restrictive. As detailed herein, modifications are possible within the scope of the appended claims without departing from the scope or essence of the present invention in its form. Although specific structures, materials, and examples have been referred to herein in detail, it is not intended to limit the present invention to the particulars disclosed herein; rather, the present invention extends to all functionally equivalent structures, methods, and uses within the scope of the appended claims.

The present invention is not limited to the embodiments described in detail above, and various modifications or changes may be made within the scope indicated in the claims of the present invention.

INDUSTRIAL APPLICABILITY

The culture method of the present invention is useful for culturing multiple samples of microorganisms.

REFERENCE SIGNS LIST

1 well
1A diameter
1B inter-well distance
1C depth
1D bottom surface
3 microchamber
3A front surface
3B back surface
11 liquid culture medium
13 microorganism
15 mixture
15A upper surface
16 water
17 plate member
19 thermostatic bath
21 stage
t1 thickness
t2 thickness

The invention claimed is:

1. A culture method for a microorganism using a plate-like microchamber having a plurality of wells on a front surface thereof, the wells being independent from each other, the method comprising:
   mixing a liquid culture medium containing agarose having a gelation temperature of no less than 5° C. and no more than 20° C. and the microorganism to obtain a mixture, and
   adjusting a mixing ratio of the liquid culture medium and the microorganism such that a turbidity of the microorganism in the mixture is 0.05 to 0.15 as measured by optical density;
   enclosing the mixture having a temperature higher than the gelation temperature of the agarose into at least one of the wells with the front surface facing upward; and keeping the microchamber in which the mixture is enclosed in the at least one of the wells at a predetermined temperature range, wherein the microchamber is hydrophilized.

2. The culture method according to claim 1, wherein a sol of the mixture is pushed into the at least one of the wells with a plate member when the mixture is enclosed into the at least one of the wells.

3. The culture method according to claim 1, wherein a bottom surface of the at least one of the wells is flat, and in checking a culture state of the microorganism, the check is made by observing the microorganism being present on the bottom surface from a back surface side of the microchamber.

4. The culture method according to claim 2, wherein a bottom surface of the at least one of the wells is flat, and in checking a culture state of the microorganism, the check is made by observing the microorganism being present on the bottom surface from a back surface side of the microchamber.

5. The culture method according to claim 1, wherein each of the wells has a circular planar shape with a diameter in a range of 350 μm to 650 μm.

6. The culture method according to claim 2, wherein the plate member is a glass plate.

* * * * *